(12) United States Patent
Takada et al.

(10) Patent No.: US 6,844,007 B2
(45) Date of Patent: Jan. 18, 2005

(54) PLASTER CONTAINING FELBINAC

(75) Inventors: Yasunori Takada, Tosu (JP); Koji Tanaka, Tosu (JP); Yasuhiro Ikeura, Tosu (JP)

(73) Assignee: Hisamitsu Pharmaceutical Co., Ltd., Saga (JP)

( * ) Notice: Subject to any disclaimer, the term of this patent is extended or adjusted under 35 U.S.C. 154(b) by 0 days.

(21) Appl. No.: 10/607,132

(22) Filed: Jun. 27, 2003

(65) Prior Publication Data

US 2004/0086554 A1 May 6, 2004

Related U.S. Application Data

(60) Division of application No. 09/859,516, filed on May 18, 2001, now Pat. No. 6,620,430, which is a continuation-in-part of application No. 09/297,643, filed as application No. PCT/JP97/04439 on Dec. 4, 1997, now abandoned.

(30) Foreign Application Priority Data

Dec. 6, 1996 (JP) ............................................. P8-342506

(51) Int. Cl.[7] ............................ A61F 13/00; A61L 15/16
(52) U.S. Cl. ......................... 424/449; 424/443; 424/448
(58) Field of Search ................................. 424/449, 443, 424/448

(56) References Cited

U.S. PATENT DOCUMENTS

| 4,455,146 A | 6/1984 | Noda et al. |
| 4,478,567 A | 10/1984 | Nakagawa et al. |
| 5,519,046 A | 5/1996 | Noda et al. |
| 5,725,874 A | 3/1998 | Oda et al. |
| 5,869,087 A | 2/1999 | Hirano et al. |

FOREIGN PATENT DOCUMENTS

| EP | 0 781 553 A1 | 7/1997 |
| JP | 4-321624 A | 11/1992 |
| JP | 5-139962 A | 6/1993 |
| JP | 8-295624 A | 11/1996 |
| WO | WO 96/08245 | 3/1996 |

OTHER PUBLICATIONS

International Search Report—PCT/JP97/04439.

*Primary Examiner*—Thurman K Page
*Assistant Examiner*—Isis Ghali
(74) *Attorney, Agent, or Firm*—Fitch, Even, Tabin & Flannery

(57) ABSTRACT

A plaster comprising a styrene-isoprene-styrene block copolymer 10–40 wt %, a rosin-based resin 5–30 wt %, a plasticizer 20–70 wt %, polyisobutylene 6–40 wt %, an antioxidant 0.1–5 wt %, and felbinac as a medicinally effective component 1.1–10 wt %, wherein the plaster does not contain crotamiton which is a solubilizer for the felbinac, the felbinac is uniformly dispersed in a semi-solubilized state in the plaster, wherein solubilized felbinac and microcrystalline felbinac coexist in the plaster, and a thickness of the plaster is 50–300 μm.

13 Claims, 2 Drawing Sheets

PLASTER CONTAINING FELBINAC

CROSS-REFERENCED APPLICATIONS

This application is a divisional of application Ser. No. 09/859,516, filed May 18, 2001, issued as U.S. Pat. No. 6,620,430 which is a continuation-in-part of application Ser. No. 09/297,643, filed May 5, 1999 now abandoned, which is the U.S. National phase of International Application PCT/JP97/04439, filed Dec. 4, 1997, and the complete disclosures of such prior applications are hereby incorporated by reference.

BACKGROUND OF THE INVENTION

1. Field of the Invention

The present invention relates to a plaster containing felbinac and, more particularly, to an anti-inflammatory, analgesic plaster containing felbinac of an anti-inflammatory, analgesic agent as a medicinally effective component for the purpose of curing lumbago, myalgia, periarthritis, and so on.

2. Related Background Art

Felbinac (4-biphenylacetic acid) is an active metabolite of fenbufen, a non-steroid type anti-inflammatory, analgesic agent, and is a drug demonstrating strong anti-inflammatory and analgesic actions. Since this drug is not suitable for oral administration, the attention has been focused on studies on preparations for dermal administration. Gels, liquids, and poultices containing the above-stated drug are commercially available hitherto. The gels and liquids, however, had problems of difficulty in administration in a given quantity, low bioavailability, adhesion to clothing, a number of administrations (for example, several administrations per day), and so on. The poultices have been developed in order to overcome these problems of the gels and liquids, but they still had problems of incapability of affixing them for a long period of time because of their weak adhesion, low bioavailability, and insufficient persistence of the effect of the drug. Japanese Patent Application Laid-Open Gazette No. Hei. 4-321624 proposed an anti-inflammatory, analgesic plaster in which the chief component of the base was a styrene-isoprene-styrene block copolymer and in which crotamiton was an essential solubilizer.

SUMMARY OF THE INVENTION

The inventors, however, found that the anti-inflammatory, analgesic plaster described in the Laid-Open Gazette No. Hei. 4-321624 was not yet satisfactory when felbinac was used as an anti-inflammatory, analgesic agent, as described below. Namely, the anti-inflammatory, analgesic plaster described in above Laid-Open Gazette No. Hei. 4-321624 was not yet satisfactory in that work steps were cumbersome because of the use of crotamiton as a solubilizer for the drug and in that secular decrease in adhesion occurred due to bleeding (percolating to the surface) of crotamiton.

Further, U.S. Pat. No. 5,725,874 proposed a plaster comprising felbinac, a styrene-isoprene-styrene block copolymer, a rosin ester derivative, a plasticizer and polyisobutylene as shown in Examples 36 and 37. However, the plaster disclosed in U.S. Pat. No. 5,725,874 comprised 3-1-menthoxypropane-1,2-diol as an essential solubilizer. The drugs (pharmaceutically effective ingredients including felbinac) in the plaster disclosed in U.S. Pat. No. 5,725,874 existed in fully solubilized or molten state. This was also apparent from the fact that the plasters of Examples 36 and 37 disclosed in U.S. Pat. No. 5,725,874 contained 3-1-menthoxypropane-1,2-diol in an amount of 5.0–7.0 wt % which was larger than that of felbinac (2.0 wt %) The plaster disclosed in U.S. Pat. No. 5,725,874 was not yet satisfactory in that the plaster was insufficient in discharge stability of the drug and in durability of the pharmacological action.

The present invention has been accomplished in view of the problems of the prior art described above and an object of the invention is to provide a plaster containing felbinac that can maintain the adhesion to skin in a high level over a long period of time, that is safe with less irritation of skin, that is excellent in stability of preparations, and that is high in release ability of the drug and excellent in the anti-inflammatory action, thus retaining the effect of the drug for a long period of time.

The inventors conducted extensive and intensive studies to achieve the above object and attained the following knowledge, thus completing the present invention. Specifically, those skilled in the art considered before that, because the drug existed in a crystalline state in the dispersion type plasters containing no solubilizer, percutaneous absorption of the drug must be small to expect the sufficient effect. In spite thereof, the present inventors found that a felbinac-containing plaster containing specific components in a specific composition and having a specific thickness, which is a dispersion type plaster containing no solubilizer and containing felbinac in a semi-solubilized state, had high drug release ability, retained the sufficient, pharmacological action for a long period of time, maintained the adhesion to skin in a high level for a long period of time, and was excellent in stability of preparations and less in the skin irritation, thus accomplishing the present invention.

The felbinac-containing plaster according to the present invention is a plaster comprising a styrene-isoprene-styrene block copolymer 10–40 wt %, a rosin-based resin 5–30 wt %, a plasticizer 20–70 wt %, polyisobutylene 6–40 wt %, an antioxidant 0.1–5 wt %, and felbinac as a medicinally effective component 1.1–10 wt %, wherein said plaster does not contain crotamiton which is a solubilizer for said felbinac, said felbinac is uniformly dispersed in a semi-solubilized state in said plaster, wherein solubilized felbinac and microcrystalline felbinac coexist in said plaster, and a thickness of said plaster is 50–300 µm.

Further, the felbinac-containing plaster according to the present invention preferably consists essentially of a styrene-isoprene-styrene block copolymer 10–40 wt %, a rosin-based resin 5–30 wt %, a plasticizer 20–70 wt %, polyisobutylene 6–40 wt %, an antioxidant 0.1–5 wt %, and felbinac as a medicinally effective component 1.1–10 wt %, wherein said plaster does not contain crotamiton which is a solubilizer for said felbinac, said felbinac is uniformly dispersed in a semi-solubilized state in said plaster, wherein solubilized felbinac and microcrystalline felbinac coexist in said plaster, and a thickness of said plaster is 50–300 µm.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that. the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
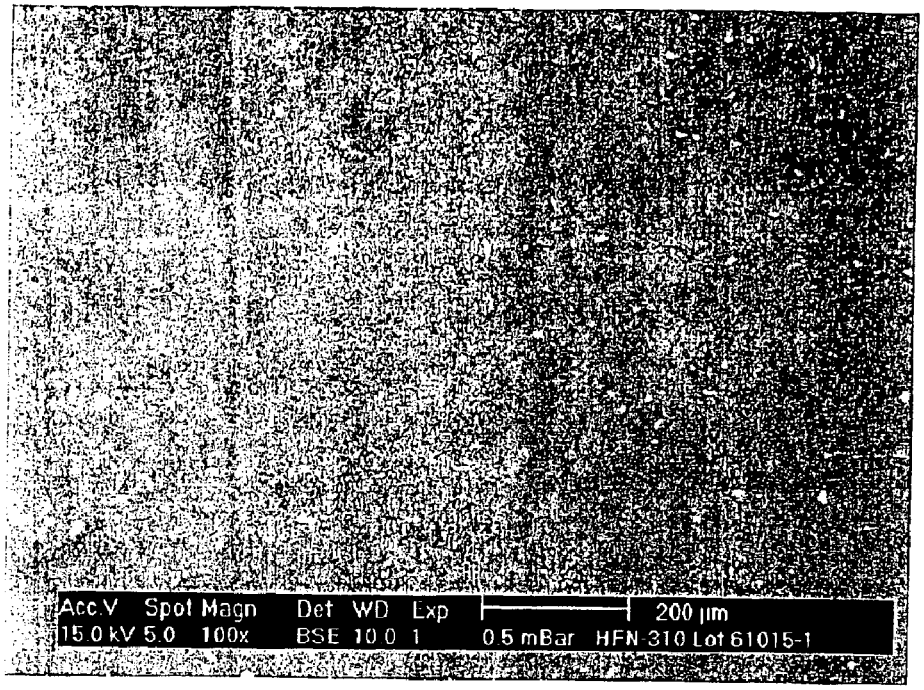
FIG. 1 is an electron microscope photograph (×100) of the plaster obtained in Example 5.

In the felbinac-containing plaster according to the present invention, felbinac as a medicinally effective component is contained in a specific blending ratio in the base containing the styrene-isoprene-styrene block copolymer, the rosin-based resin, the plasticizer, polyisobutylene and the antioxidant in specific blending ratios, respectively. First, the various base components used for forming the plaster of the present invention will be described in detail.

The styrene-isoprene-styrene block copolymer according to the present invention is a block copolymer of styrene and isoprene and has polystyrene chains at the both ends, and this styrene-isoprene-styrene block copolymer can be selected from Califlex TR-1107, TR-1111, TR-1112 or TR-1117 (trade names, available from Shell Kagaku K.K.), JSR SIS-5000 or 5002 (trade names, available from Japan Synthetic Rubber Co., Ltd.), Quintac 3530 or 3421 (trade names, available from Nippon Zeon Co., Ltd.), Solprene 428 (trade name, available from Phillips Petroleum International Ltd.), and so on, which can be used singly or in a combination of two or more species.

A blending ratio of the styrene-isoprene-styrene block copolymer is 10–40 wt % and preferably 15–35 wt % of the whole plaster. This range of blending ratio demonstrates great improvements in stability of preparations (the plaster), adhesive strength (tackiness), the adhesion to skin in the long term (adhesion persistence), percutaneous absorption of the drug, dispersibility of the drug, pain upon stripping, the rate of occurrence of eruptions in the skin, and so on. In a case where the above blending ratio is lower than 10 wt %, cohesive force and shape retention of the base will degrade. On the other hand, blending ratios over 40 wt % will cause reduction in adhesive strength, nonuniformity of ointment (plaster), and degradation of workability.

The rosin-based resin according to the present invention is a resin containing rosin or a rosin derivative as a base material, and those suitably applicable are rosin esters, hydrogenated rosin esters, maleic rosins, and so on. The rosin-based resin can be selected from Ester Gum A, AA-G, H or HP (trade names, available from Arakawa Chemical Industries Ltd.), Hariester L, S or P (trade names, available from Arakawa Chemical Industries Ltd.), Pinecrystal KE-100 (trade name, available from Arakawa Chemical Industries Ltd.), KE-311 (trade name, available from Arakawa Chemical Industries Ltd.), Hercolyn D (trade name, available from Rika-Hercules Inc.), Foral 85 or 105 (trade names, available from Rika-Hercules Inc.), Stebelite Ester 7 or 10 (trade names, available from Rika-Hercules Inc.), Pentalyn 4820 or 4740 (trade names, available from Rika-Hercules Inc.), and so on, which can be used singly or in a combination of two or more species.

A blending ratio of the above rosin-based resin is 5–30 wt % and preferably 10–25 wt % of the whole plaster. This range of blending ratio exhibits great improvements in the stability of preparations, adhesive strength, adhesion persistence, percutaneous absorption of the drug, dispersibility of the drug, pain upon stripping, the rate of occurrence of eruptions in the skin, and so on. Blending ratios below 5 wt % will degrade the adhesive strength, adhesion persistence, and dispersibility of the drug and cause nonuniformity of ointment and degradation of workability due to increase in the viscosity of ointment. On the other hand, blending ratios over 30 wt % will degrade the percutaneous absorption of the drug and shape retention and will increase the pain upon stripping, the rate of occurrence of eruptions in the skin, stickiness, and so on.

The plasticizer according to the present invention is an agent compatible with the other base components and capable of providing the base with flexibility, and suitably applicable plasticizers are almond oil, olive oil, tsubaki oil, persic oil, peanut oil, olefin acids, liquid polyisoprene, liquid polybutene, liquid paraffin, and so on. These plasticizers may be used singly or in a combination of two or more species and among them the liquid paraffin is particularly preferred.

A blending ratio of the above plasticizer is 20–70 wt % and preferably 30–60 wt % of the whole plaster. This range of blending ratio exhibits great improvements in the stability of preparations, adhesive strength, adhesion persistence, percutaneous absorption of the drug, dispersibility of the drug, pain upon stripping, the rate of occurrence of eruptions in the skin, and so on. Blending ratios below 20 wt % will degrade the adhesive strength, percutaneous absorption of the drug, and dispersibility of the drug and will cause nonuniformity of ointment and degradation of workability due to increase in the viscosity of ointment. On the other hand, blending ratios over 70 wt % will degrade the stability of preparations, cohesive force, and shape retention and will increase the pain upon stripping, stickiness, and so on.

The plaster of the present invention further comprises polyisobutylene, in addition to the aforementioned styrene-isoprene-styrene block copolymer, rosin-based resin, plasticizer, and felbinac, and thus it may be substantially comprised of the styrene-isoprene-styrene block copolymer, rosin-based resin, plasticizer, polyisobutylene, and felbinac.

The polyisobutylene according to the present invention is a polymer of isobutylene and the polyisobutylene is selected from Opanol B-3, B-10, B-15, B-50, B-100 or B-200 (tradenames, available from BASFAG), Vistanex LM-MS, LM-MH, MML-80, MML-100, MML-120 or MML-140 (trade names, available from Exxon Chemical Japan Ltd.), Tetrax 3T, 4T, 5T or 6T (trade names, available from Nippon Petrochemicals Co., Ltd.), and so on, which can be used singly or in a combination of two or more species.

A blending ratio of the above polyisobutylene is 6–40 wt % and preferably 6.5–20 wt % of the whole plaster. This range of blending ratio will reveal improvements in the stability of preparations, adhesive strength, adhesion persistence, percutaneous absorption of the drug, dispersibility of the drug, pain upon stripping, the rate of occurrence of eruptions in the skin, and so on. Blending ratios below 6 wt % will tend to degrade the adhesive strength and adhesion persistence and increase the pain upon stripping and the rate of occurrence of eruptions in the skin. On the other hand, blending ratios over 40 wt % will tend to degrade the shape retention and increase the stickiness.

The plaster of the present invention further contain an antioxidant, in addition to the aforementioned styrene-isoprene-styrene block copolymer, rosin-based resin, plasticizer, felbinac and polyisobutylene. Accordingly, the plaster of the present invention may be substantially comprised of the styrene-isoprene-styrene block copolymer, rosin-based resin, plasticizer, polyisobutylene, antioxidant, and felbinac.

The antioxidant according to the present invention is selected from ascorbic acid, propyl gallate, butylhydroxyanisole, dibutylhydroxytoluene (BHT), nordihydroguaiaretic acid, tocopherol, tocopherol acetate, and so on.

A blending ratio of the antioxidant is 0.1–5 wt % and preferably 0.5–2 wt % of the whole plaster. Blending ratios below the lower limit will tend to cause deterioration of the base with a lapse of time and increase remainder of ointment, stickiness, and soon. On the other hand, blending ratios over the upper limit will tend to degrade the cohesive force of preparations and the shape retention and increase the pain upon stripping, stickiness, and so on.

In the plaster of the present invention, felbinac as a medicinally effective component, i.e., 4-biphenylacetic acid, is contained in the specific blending ratio in the base containing the aforementioned styrene-isoprene-styrene block copolymer, rosin-based resin, plasticizer, polyisobutylene and antioxidant. The blending ratio of felbinac in the plaster of the present invention is 1.1–10 wt %, preferably 2–8 wt %, and particularly preferably 3–7 wt % of the whole plaster. This range of blending ratio will exhibit great improvements in the percutaneous absorption of the drug, persistence of the effect of the drug, dispersibility of the drug, and so on. Blending ratios below 1.1 wt % will degrade the percutaneous absorption of the drug and persistence of the effect of the drug and fail to achieve the sufficient effect of the drug. On the other hand, blending ratios over 10 wt % will degrade the dispersibility of the drug and cause the nonuniformity of ointment.

The plaster of the present invention contains the felbinac described above, but does not contain any crotamiton, which is a solubilizer used to be conventionally considered as an essential component. Namely, the plaster of the present invention contains the aforementioned styrene-isoprene-styrene block copolymer, rosin-based resin, plasticizer, polyisobutylene, antioxidant and felbinac and does not contain any crotamiton being the solubilizer for the felbinac, and it may be substantially comprised of the styrene-isoprene-styrene block copolymer, rosin-based resin, plasticizer, polyisobutylene, antioxidant and felbinac.

Since the felbinac-containing plaster of the present invention contains no crotamiton of solubilizer as described above, secular decrease in adhesive strength will not occur due to the bleeding of crotamiton and it is free of cumbersome work steps caused by use thereof. The felbinac-containing plaster of the present invention preferably contains none of solubilizers for felbinac at all; that is, the plaster, preferably, does not contain any agent capable of apparently dissolving felbinac over its solubility in the base at all. When the plaster does not contain any other plasticizer than crotamiton, either, as described, there is such a tendency as to prevent occurrence of secular decrease in adhesive strength due to bleeding of solubilizer more certainly. Examples of such solubilizers other than crotamiton are benzyl alcohol and diisopropanolamine.

Although the plaster of the present invention having the above composition does not contain crotamiton being the solubilizer described above, felbinac is not taken in a perfectly crystalline state into the base, but it is uniformly dispersed in a semi-solubilized (semi-molten) state in the base, wherein solubilized felbinac and microcrystalline felbinac coexist in the plaster. This dispersion provides substantial benefits, because as the partially solubilized drug (felbinac) is discharged from the base, the uniformly dispersed drug in the crystalline state will be dissolved into the base as occasion demands. This provides stable discharge of the drug at constant speed over a long time in the plaster of the present invention. Therefore, although the drug does not exist in the fully solubilized state with the solubilizer in the base, different from the solubilizer-containing plaster described in the Laid-Open Gazette No. Hei. 4-321624, the felbinac-containing dispersion type plaster of the present invention provides high releasing ability of the drug and retains sufficient pharmacological action (an anti-inflammatory action) over a long time.

In the plaster of the present invention, a ratio of microcrystalline felbinac is preferably 20–80 wt % of the whole felbinac (the total amount of solubilized felbinac and microcrystalline felbinac), at least in an initial state.

The plaster of the present invention may further contain, if desired, another (other) additive component(s) such as an inorganic filler, a synthetic polymer, a tackifier, an ultraviolet light absorber, an antihistamic agent, an antibacterial agent, or a perfume, in addition to the aforementioned styrene-isoprene-styrene block copolymer, rosin-based resin, plasticizer, felbinac, and, if necessary, the polyisobutylene.

The further additive component described above is selected from inorganic fillers (aluminum hydroxide, aluminum silicate hydrate, synthetic aluminum silicate, kaolin, titanium oxide, talc, zinc oxide, silica hydrate, magnesium carbonate, calcium hydrogenphosphate, magnesium silicate, diatomaceous earth, silicic anhydride, bentonite, etc.), synthetic polymers (polyacrylic polymers, synthetic polyisoprene rubbers, polystyrenes, polybutadiene rubbers, silicone rubbers, styrene-butylene-styrene block copolymers, styrene-isoprene block copolymers, etc.), tackifiers (terpene resins, petroleum resins, etc.), ultraviolet light absorbers (paraminobenzoic acid, paraminobenzoic ester, amyl paradimethylaminobenzoate, salicylic ester, methyl anthranilate, umbelliferone, esculin, benzyl cinnamate, cinoxate, guaiazulene, urocanic acid, 2-(2-hydroxy-5-methyphenyl) benzotriazole, 4-methoxybenzophenone, 2-hydroxy-4-methoxybenzophenone, octabenzone, dioxybenzone, dihydroxydimethoxybenzophenone, sulisobenzone, benzoresorsinol, octyl dimethylparamino benzoate, ethylhexyl p-methoxy-cinnamate, etc.), antihistamines (isopentyl chloride, diphenhydramine hydrochloride, iproheptine hydrochloride, diphenylpyraline hydrochloride, cyproheptadine hydrochloride, triprolidine hydrochloride, promethazine hydrochloride, homochlorcyclizine hydrochloride, alimemazine tartrate, diphenhydramine tannate, diphenylpyraline piprinhydrinate, clemastine fumarate, chlorpheniramine meleate, dimethindene maleate, mequitazine, etc.), antibacterial agents (paraoxybenzoic ester, benzoic acid, benzoate, salicylate, sorbic acid, sorbate, dehydroacetate, 4-isopropyl-3-methylphenol, 2-isopropyl-5-methylphenol, hinokitiol, cresol, 2,4,4-trichloro-2'-hydroxydiphenylether, 3,4,4'-trichlorocarbanilide, chlorobutanol, benzalkonium chloride, benzethonium chloride, etc.), refrigerants or perfumes (1-menthol, etc.), and so on.

A blending ratio of such further additive component is preferably 0.01–7 wt % and more preferably 0.1–5 wt % of the whole plaster. Blending ratios below the lower limit will tend to cause deterioration of the base with a lapse of time and increase remainder of ointment, stickiness, and so on. On the other hand, blending ratios over the upper limit will tend to degrade the cohesive force of preparations and the shape retention and increase the pain upon stripping, stickiness, and so on.

The thickness (not including thicknesses of a backing and a released liner described hereinafter) of the plaster (the plaster layer) of the present invention prepared using the above components is 50–300 μm and preferably 80–200 μm. When the thickness is determined in this range, great improvements are achieved in the adhesive strength, cohesive force, adhesion persistence, pain upon stripping, and so on. In a case where the above thickness is less than 50 μm, the adhesive strength and adhesion persistence will degrade. On the other hand, in a case where the above thickness is over 300 μm, the cohesive force and shape retention will degrade.

The plaster of the present invention as described above is highly flexible and freely expands and contracts longitudinally and laterally. Since the plaster of the present invention has the excellent adhesion and high expansion rate as described, it permits use of a highly flexible backing (support), which was hardly used for the conventional solubilizer-containing plasters, and it achieves the affixing feeling of high level.

The felbinac-containing plaster of the present invention described above has various excellent characteristics below.

1) Since the plaster is an oil-based plaster, it has excellent adhesion and it can be affixed to even a bending portion such as an elbow or a knee over a long period of time without peeling off.
2) Since the drug is dispersed in a concentration over the solubility thereof in the semi-solubilized state, the expected effect of the drug appears over a long period of time.
3) Since the plaster has the oil base containing no water, it has an excellent heat reserving effect of affixed portion and can be used for chronic inflammation and the like.
4) Since the plaster is made without using any solubilizer, absorbefacient agent, or the like, the work steps are easy and simple, and secular stability of preparations is also excellent.
5) The oil-based plaster allows the thickness to be decreased and is excellent in fit feeling when affixed.
6) The adhesive strength of the conventional solubilizer-containing plasters was not sufficient, and the size thereof was limited to approximately 80 cm$^2$ or less. In contrast with it, the plaster of the present invention has the extremely high adhesive strength, because it contains no solubilizer. Therefore, the size of the present plaster can be 100 cm$^2$ or more. The plaster of the present invention can be made in the size equivalent to that of the conventional poultices as described, and it is superior in the adhesive strength and flexibility to the poultices.

The plaster of the present invention described above is preferably spread on a backing (support). The backing is desirably one not affecting discharge of the drug from the plaster of the present invention and can be flexible or non-flexible. The backing applicable to the present invention is one selected from a film, a sheet, a sheet porous body, a sheet foam, and a woven or nonwoven fabric of a synthetic resin such as polyethylene, polypropylene, polybutadien, an ethylene-vinyl acetate copolymer, polyvinyl chloride, a polyester, a polyamide, or a polyurethane; paper; fabric; nonwoven fabric; a lamination thereof, and so on.

Among these plaster backings, a backing with flexibility is preferred and a stretch polyester fabric is particularly suitable. The stretch polyester fabric is preferably one exhibiting the longitudinal strength of 200 g to 3 kg and the lateral strength of 100 g to 600 g in the 30%-modulus (tensile strength) test under such measurement conditions that the sample width is 50 mm, the sample length 200 mm, and the elongation strength 200 mm/min. Further, the basic weight (weight per unit area) of the backing according to the present invention is preferably 100±30 g/m$^2$.

Since the plaster of the present invention has the high expansion rate as described above, it becomes possible to use the backing with high flexibility, which was hardly used for the conventional solubilizer-containing plasters, and particularly preferably to use the stretch polyester fabric. Use of the polyester fabric with flexibility as described tends to make the plaster of the present invention superior in the following respects. Specifically, i) the conventional solubilizer-containing plasters, when affixed to a bending portion such as a joint to move heavily, were easy to peel off because of the motion. In contrast with it, in the plaster of the present invention, the polyester fabric can expand and contract longitudinally and laterally in accordance with the motion of skin, so that the plaster is firmly affixed with less stretched feeling and over a long time. ii) Since the polyester fabric has moderate flexibility, the plaster is easy to affix and easy to strip. iii) The anchoring effect is enhanced (the ointment permeates the backing and the adhesive strength is retained), and the flexibility is retained.

A preferred example of a method for preparing the felbinac-containing plaster of the present invention will be described below.

First, a styrene-isoprene-styrene block copolymer, a rosin-based resin, a plasticizer, polyisobutylene and an antioxidant (other additive components, etc. if any) are mixed each in predetermined percentage to obtain a mixture, and the mixture is heated and stirred under an inert atmosphere of nitrogen or the like, thus obtaining a dissolved substance. The temperature upon stirring is preferably 110–200° C. and the stirring time is preferably 30–120 minutes. Subsequently, felbinac of the effective component is added to the above dissolved substance and the mixture is stirred preferably at 110–200° C. and preferably for 5–30 minutes, thereby obtaining a uniform dispersion.

Then this dispersion is spread directly over the backing (support) by an ordinary method and thereafter is covered by a released liner (peeling cover); or, it is also possible to once spread this dispersion over the released liner, thereafter place them on the backing, and press and transfer the dispersion onto the backing. The released liner of this type is selected from released paper processed by a release treatment (a treatment for facilitating release); cellophane; or a plastic film of polyethylene, polypropylene, polyester, or the like; and so on. The above preparation method allows us to obtain the plaster of the present invention in which felbinac is uniformly dispersed in the semi-solubilized state in the base.

It should be noted that only one embodiment was described of the order of blending of the respective base components, the medicinally effective component, and the other additive components in the above preparation method and that the preparation method of the plaster of the present invention is not limited to this method of the blending order.

EXAMPLES

The felbinac-containing plaster of the present invention will be described in more detail with examples and comparative examples, but it should be noted that the felbinac-containing plaster of the present invention is not limited to those described in the following examples. In the examples and comparative examples, "part(s)" and "%" mean "part(s) by weight" and "% by weight", respectively, unless otherwise stated specifically.

Example 1

| | |
|---|---|
| styrene-isoprene-styrene block copolymer (trade name: Califlex TR-1107) | 25.0 parts |
| liquid paraffin | 47.0 parts |
| rosin-based resin (trade name: Ester Gum H) | 12.0 parts |
| polyisobutylene (trade name: Opanol B-10) | 10.0 parts |
| dibutylhydroxytoluene | 1.0 part |
| felbinac | 5.0 parts |

The plaster was prepared in the above formulation according to the aforementioned preparation method. Specifically, the components other than felbinac in the above formulation were mixed to obtain a mixture and the mixture was stirred at 130–180° C. under the nitrogen atmosphere for 40–90 minutes to obtain a dissolved substance. Subsequently, felbinac which is the medicinally effective component was added into the dissolved substance and the mixture was stirred at 130–180° C. for 3–20 minutes to obtain a uniform dispersion. Then this dispersion was spread over the backing (fabric of polyester) so that the thickness of the plaster layer obtained was 50 μm. Thereafter, the dispersion was covered by the released liner (polyester film) and the product after cooled was cut in the desired size, thereby obtaining the dispersion type plaster in which felbinac was uniformly dispersed in the semi-solubilized state. The polyester fabric used was one having the longitudinal strength of 210–300 g and the lateral strength of 100–170 g in the 30%-modulus test (the sample width 50 mm, the sample length 200 mm, and the elongation strength 200 mm/min, using Autograph AGS-100B (available from Shimadzu Corporation), and having the basic weight of 110±20 g/m².

Example 2

| | |
|---|---|
| styrene-isoprene-styrene block copolymer (trade name: Califlex TR-1111) | 30.0 parts |
| liquid paraffin | 39.0 parts |
| rosin-based resin (trade name: Pinecrystal KE-100) | 20.0 parts |
| polyisobutylene (trade name: Opanol B-50) | 6.0 parts |
| dibutylhydroxytoluene | 1.0 part |
| felbinac | 4.0 parts |

The plaster was prepared in the same manner as in Example 1 except that the formulation was changed to the above formulation and that the thickness of the plaster layer was 100 μm, obtaining the dispersion type plaster in which felbinac was uniformly dispersed in the semi-solubilized state.

Example 3

| | |
|---|---|
| styrene-isoprene-styrene block copolymer (trade name: Califlex TR-1112) | 20.0 parts |
| liquid paraffin | 46.0 parts |
| rosin-based resin (trade name: Stebelite Ester 7) | 15.0 parts |
| polyisobutylene (trade name: Opanol B-100) | 15.0 parts |
| dibutylhydroxytoluene | 1.0 part |
| felbinac | 3.0 parts |

The plaster was prepared in the same manner as in Example 1 except that the formulation was changed to the above formulation and that the thickness of the plaster layer was 140 μm, obtaining the dispersion type plaster in which felbinac was uniformly dispersed in the semi-solubilized state.

Example 4

| | |
|---|---|
| styrene-isoprene-styrene block copolymer (trade name: Califlex TR-1117) | 23.0 parts |
| liquid paraffin | 40.0 parts |
| rosin-based resin (trade name: KE-311) | 25.0 parts |
| polyisobutylene (trade name: Opanol B-200) | 8.0 parts |
| dibutylhydroxytoluene | 1.0 part |
| felbinac | 3.0 parts |

The plaster was prepared in the same manner as in Example 1 except that the formulation was changed to the above formulation and that the thickness of the plaster layer was 300 μm, obtaining the dispersion type plaster in which felbinac was uniformly dispersed in the semi-solubilized state.

Example 5

| | |
|---|---|
| styrene-isoprene-styrene block copolymer (trade name: JSR SIS-5000) | 20.0 parts |
| liquid paraffin | 41.0 parts |
| rosin-based resin (trade name: Foral 105) | 15.0 parts |
| polyisobutylene (trade name: Vistanex LM-MS) | 20.0 parts |
| dibutylhydroxytoluene | 1.0 part |
| felbinac | 3.0 parts |

Figure 2:
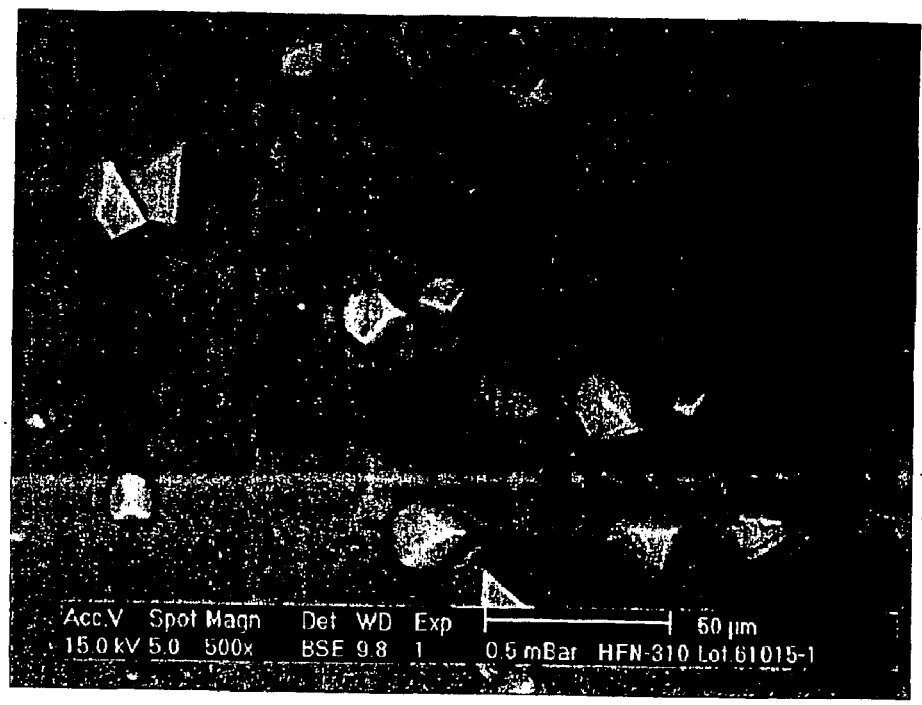
FIG. 2 is an electron microscope photograph (×500) of the plaster obtained in Example 5.

The plaster was prepared in the same manner as in Example 1 except that the formulation was changed to the above formulation and that the thickness of the plaster layer was 200 μm, obtaining the dispersion type plaster in which felbinac was uniformly dispersed in the semi-solubilized state. Electron microscope photographs (×100 and ×500) of the plaster obtained in Example 5 are shown as FIGS. 1 and 2.

Example 6

| | |
|---|---|
| styrene-isoprene-styrene block copolymer (trade name: JSR SIS-5002) | 15.0 parts |
| liquid paraffin | 58.0 parts |
| rosin-based resin (trade name: Stebelite 10) | 15.0 parts |

-continued

| | |
|---|---|
| polyisobutylene (trade name: Vistanex LM-MH) | 7.0 parts |
| dibutylhydroxytoluene | 1.0 part |
| felbinac | 4.0 parts |

The plaster was prepared in the same manner as in Example 1 except that the formulation was changed to the above formulation and that the thickness of the plaster layer was 80 µm, obtaining the dispersion type plaster in which felbinac was uniformly dispersed in the semi-solubilized state.

Example 7

| | |
|---|---|
| styrene-isoprene-styrene block copolymer (trade name: Quintac 3530) | 35.0 parts |
| liquid paraffin | 35.0 parts |
| rosin-based resin (trade name: Foral 85) | 15.0 parts |
| polyisobutylene (trade name: Vistanex MML-140) | 10.0 parts |
| dibutylhydroxytoluene | 1.0 part |
| felbinac | 4.0 parts |

The plaster was prepared in the same manner as in Example 1 except that the formulation was changed to the above formulation and that the thickness of the plaster layer was 160 µm, obtaining the dispersion type plaster in which felbinac was uniformly dispersed in the semi-solubilized state.

Example 8

| | |
|---|---|
| styrene-isoprene-styrene block copolymer (trade name: Quintac 3421) | 25.0 parts |
| liquid paraffin | 30.0 parts |
| rosin-based resin (trade name: Pentalyn 4820) | 22.0 parts |
| polyisobutylene (trade name: Tetrax 3T) | 15.0 parts |
| dibutylhydroxytoluene | 1.0 part |
| felbinac | 7.0 parts |

The plaster was prepared in the same manner as in Example 1 except that the formulation was changed to the above formulation and that the thickness of the plaster layer was 120 µm, obtaining the dispersion type plaster in which felbinac was uniformly dispersed in the semi-solubilized state.

Example 9

| | |
|---|---|
| styrene-isoprene-styrene block copolymer (trade name: Solprene 428) | 25.0 parts |
| liquid paraffin | 36.0 parts |
| rosin-based resin (trade name: Hercolyn D) | 25.0 parts |
| polyisobutylene (trade name: Tetrax 5T) | 7.5 parts |
| dibutylhydroxytoluene | 1.0 part |
| 1-menthol | 0.5 part |
| felbinac | 5.0 parts |

The plaster was prepared in the same manner as in Example 1 except that the formulation was changed to the above formulation and that the thickness of the plaster layer was 160 µm, obtaining the dispersion type plaster in which felbinac was uniformly dispersed in the semi-solubilized state.

Example 10

| | |
|---|---|
| styrene-isoprene-styrene block copolymer (trade name: Quintac 3421) | 15.0 parts |
| liquid paraffin | 40.0 parts |
| rosin-based resin (trade name: Hariester L) | 10.0 parts |
| polyisobutylene (trade name: Tetrax 6T) | 30.0 parts |
| dibutylhydroxytoluene | 1.0 part |
| 1-menthol | 1.0 part |
| felbinac | 3.0 parts |

The plaster was prepared in the same manner as in Example 1 except that the formulation was changed to the above formulation and that the thickness of the plaster layer was 180 µm, obtaining the dispersion type plaster in which felbinac was uniformly dispersed in the semi-solubilized state.

Example 11

The plaster was prepared in the same manner as in Example 9 except that the polyisobutylene was excluded from the formulation.

Example 12

The plaster was prepared in the same manner as in Example 3 except that the thickness of the plaster layer was 50 µm.

Example 13

The plaster was prepared in the same manner as in Example 3 except that the thickness of the plaster layer was 80 µm.

Example 14

The plaster was prepared in the same manner as in Example 3 except that the thickness of the plaster layer was 200 µm.

Example 15

The plaster was prepared in the same manner as in Example 3 except that the thickness of the plaster layer was 300 µm.

Comparative Example 1

| | |
|---|---|
| styrene-isoprene-styrene block copolymer (trade name: Califlex TR-1112) | 20.0 parts |
| liquid paraffin | 52.0 parts |
| rosin-based resin (trade name: KE-311) | 15.0 parts |
| polyisobutylene (trade name: Tetrax 4T) | 5.0 parts |
| dibutylhydroxytoluene | 2.0 parts |
| crotamiton | 5.0 parts |
| felbinac | 1.0 part |

The plaster was prepared in the same manner as in Example 5 except that the formulation was changed to the above formulation, i.e., that crotamiton was mixed as a solubilizer for felbinac, thus obtaining a dissolution type plaster in which felbinac existed in a fully solubilized state because of the solubilizer. In this comparative example, felbinac was dissolved in crotamiton and then the mixture was added into the aforementioned dissolved substance.

Comparative Example 2

The plaster was prepared in the same manner as in Example 5 except that felbinac being the medicinally effective component was excluded from the formulation.

Comparative Example 3

The plaster was prepared in the same manner as in Example 3 except that the thickness of the plaster layer was 30 µm.

Comparative Example 4

The plaster was prepared in the same manner as in Example 3 except that the thickness of the plaster layer was 350 µm.

Test Example 1
(Stability Test: Adhesive Strength)

The plasters obtained in Examples 3, 5, 7 and 10 and Comparative Example 1 were evaluated in the following manner as to the stability of adhesive strength. The adhesive strength of each plaster (the size: 10 cm×14 cm) was measured by the probe tack test method (machine used: PROVE TACK TESTER) immediately after the preparation (in the initial stage), after 3-month storage at 40° C., and after 6-month storage at 40° C. The results obtained are shown in Table 1.

TABLE 1

| Example · Comparative | Adhesive strength (g) | | |
|---|---|---|---|
| Example | Initial | 40° C., 3 months | 40° C., 6 months |
| Example 3 | 54.3 | 52.4 | 55.3 |
| Example 5 | 55.7 | 55.9 | 53.1 |
| Example 7 | 50.2 | 49.5 | 49.0 |
| Example 10 | 45.2 | 47.3 | 47.0 |
| Comparative Example 1 | 51.5 | 42.8 | 30.7 |

As apparent from the results shown in Table 1, the plasters obtained in Examples 3, 5, 7 and 10 had good stability of adhesive strength, but the plaster obtained in Comparative Example 1 showed secular decrease of adhesive strength due to bleeding of crotamiton.

Test Example 2
(Stability Test: Hairless Mouse Skin Permeation Experiment)

The hairless mouse skin permeation test was conducted in the following manner, using the plasters obtained in Example 5 and Comparative Example 1 immediately after the preparation and after 6-month storage at 40° C. Specifically, the plaster cut in the diameter of 10 mm was affixed to the skin of the back peeled off of a hairless mouse (female, 7 week old) and the lamination was set in a flow through type cell with the dermis side being the receptor phase. A receptor liquid (phosphate buffer of pH 7.4) was allowed to flow at the flow rate of 0.8 ml/hr and an amount of felbinac permeating into the receptor liquid was measured by use of HPLC. The results obtained are shown in FIG. 3.

Figure 3:
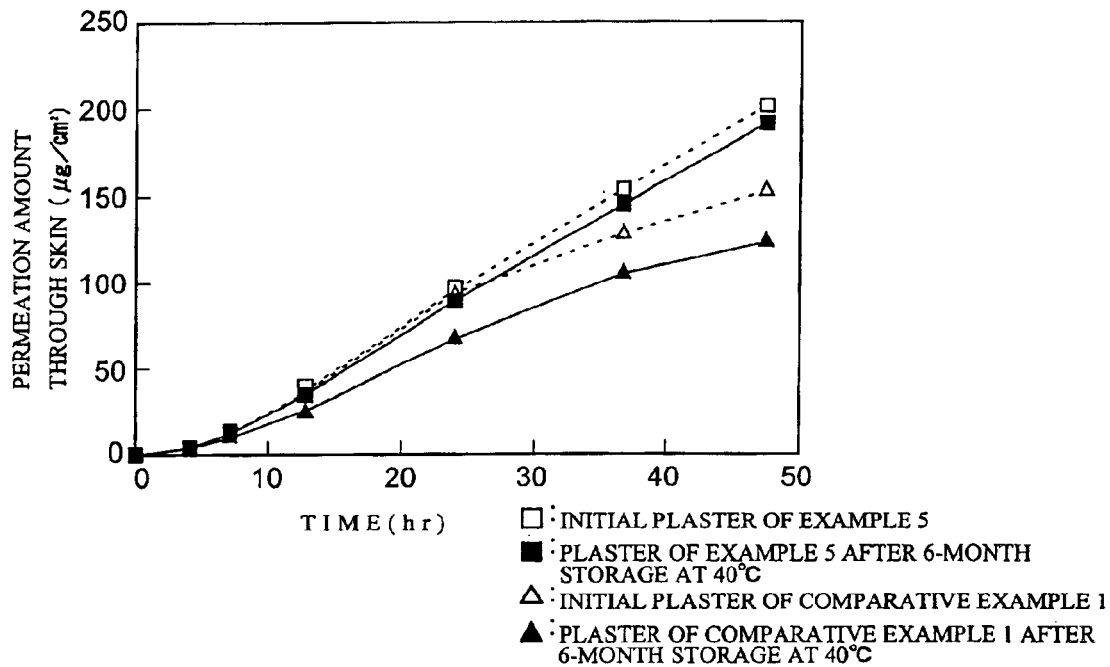
FIG. 3 is a graph to show the results of skin permeation experiment using hairless mice.

As apparent from the results shown in FIG. 3, the plaster obtained in Example 5 revealed the stable drug release ability even after the 6-month storage at 40° C., and the drug release ability was stably retained over a long period of time as against the plaster obtained in Comparative Example 1.

Test Example 3
(Carrageenin-Induced Paw Edema Experiment)

Figure 4:
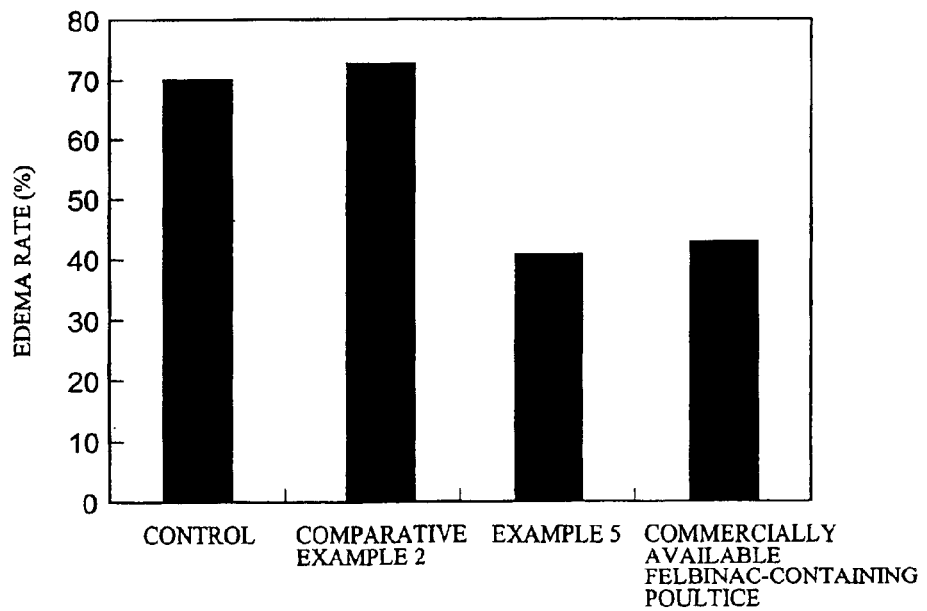
FIG. 4 is a graph to show the results of carrageenin-induced paw edema experiment in rabbits.

Male rats of Wister strain weighing approximately 135 g were used as test animals in groups each consisting of fifteen rats. Test samples were the plaster obtained in Example 5, the plaster obtained in Comparative Example 2, and a felbinac-containing poultice commercially available (trade name: Seltouch, available from Lederle Japan Ltd.) each cut in the size of 3 cm×4 cm. Each of the plasters (or the poultice) was affixed to the rear right paw of rat for four hours and thereafter was removed. Immediately thereafter, 0.1 ml of 1% carrageenin solution was subcutaneously injected into the same portion to induce the reaction. The volume of paw was measured 3 hours after the induction of the reaction and an edema rate was calculated based on the volume of paw before the injection. The results obtained are shown in FIG. 4. The control is an example obtained without affixing the plaster (or the poultice) to the rat.

As apparent from the results shown in FIG. 4, the plaster obtained in Comparative Example 2 containing no felbinac showed no effect on the carrageenin-induced paw edema, whereas the plaster obtained in Example 5 demonstrated the strong anti-inflammatory action, the effect of which was equivalent to that of the commercially available felbinac-containing poultice.

Test Example 4
(Adhesion Test)

The plasters (the size of 10 cm×14 cm) obtained in Example 9 and Example 11 were respectively affixed to the left and right knees of 30 healthy male and female adults, and the adhesion and pain upon stripping was checked about 6 hours later according to the following criteria.

| [Criteria] | |
|---|---|
| Adhesion | |
| perfect adhesion | 5 points |
| partial peeling of corner | 4 points |
| peeling of one third or more | 3 points |
| peeling of a half or more | 2 points |
| complete drop | 1 point |
| Pain upon stripping | |
| no pain | 5 points |
| little pain | 4 points |
| slight pain | 3 points |
| pain | 2 points |
| heavy pain | 1 point |

Averages of scores of the 30 adults are shown in Table 2.

TABLE 2

| Example | Adhesion | Pain upon stripping |
|---|---|---|
| Example 9 | 4.6 | 4.4 |
| Example 11 | 3.9 | 2.8 |

As apparent from the results shown in Table 2, the plasters obtained in Example 9 and Example 11 both demonstrated good adhesion, but the plaster obtained in Example 9 has better adhesion and gives less pain upon stripping and thus can be said as a plaster very excellent in use.

Test Example 5
(Adhesion Test)

Each of the plasters (the size 10 cm×14 cm) obtained in Examples 3, 12, 13, 14 and 15 and Comparative Examples 3 and 4 was affixed to the knees of 30 healthy male and female adults, and the adhesion was checked about 6 hours later according to the following criteria.

| [Criteria] | |
|---|---|
| Adhesion | |
| perfect adhesion | 5 points |
| partial peeling of corner | 4 points |
| peeling of one third or more | 3 points |
| peeling of a half or more | 2 points |
| complete drop | 1 point |

Averages of scores of the 30 adults are shown in Table 3.

Test Example 6
(Stability Test: Shape Retention)

The plasters (the size 10 cm×14 cm) obtained in Examples 3, 12, 13, 14 and 15 and Comparative Examples 3 and 4 each were stored at 50° C. for two months and thereafter their shape was evaluated according to the following criteria.

[Criteria]
good shape retained: ○
slight overflow of ointment observed: Δ
heavy overflow of ointment observed: X The results obtained are shown in Table 3.

TABLE 3

| Example · Comparative Example | Adhesion | Shape |
|---|---|---|
| Example 3 | 4.5 | ○ |
| Example 12 | 3.1 | ○ |
| Example 13 | 3.8 | ○ |
| Example 14 | 4.2 | ○ |
| Example 15 | 4.1 | Δ |
| Comparative Example 3 | 2.3 | ○ |
| Comparative Example 4 | 3.7 | X |

As apparent from the results shown in Table 3, the plasters obtained in Examples 3, 12, 13, 14 and 15 showed the good results of both the adhesion and the shape after the 2-month storage at 50° C., whereas the plaster obtained in Comparative Example 3 revealed insufficient adhesion and the plaster obtained in Comparative Example 4 demonstrated insufficient shape retention after the 2-month storage at 50° C.

As described above, the present invention can achieve the felbinac-containing plaster that retains the high drug release capability and sufficient pharmacological action (the anti-inflammatory action) over a long period, though it is the dispersion type plaster containing no crotamiton of solubilizer, that retains the adhesion to skin in the high level over a long period, that is excellent in the stability of preparations, and that gives little skin irritation.

Accordingly, the present invention can provide the felbinac-containing plaster useful as an anti-inflammatory, analgesic plaster for external application.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A plaster comprising 10–40 wt % of a styrene-isoprene-styrene block copolymer, 5–30 wt % of a rosin-based resin, 20–70 wt % of a plasticizer, 0.01–7 wt % of 1-menthol, and 1.1–10 wt % of felbinac as a medicinally effective component, wherein said plaster does not contain a solubilizer for said felbinac, said felbinac is uniformly dispersed in a semi-solubilized state in said plaster, solubilized felbinac and microcrystalline felbinac coexist in said plaster, and said plaster has a thickness of 50–300 μm.

2. A plaster according to claim 1, further comprising a backing made of a stretch polyester fabric.

3. A plaster according to claim 2, wherein said stretch polyester fabric is one demonstrating a longitudinal strength of 200 g to 3 kg and a lateral strength of 100 g to 600 g in a 30%-modulus test under measurement conditions of sample width 50 mm, sample length 200 mm, and elongation strength 200 mm/min.

4. A plaster according to claim 2, wherein a basic weight of said backing is 100±30 g/m².

5. A plaster according to claim 1, wherein a blending ratio of said felbinac is 3–7 wt % of the whole plaster.

6. A plaster according to claim 1, wherein a blending ratio of the whole plaster for the following is: said styrene-isoprene-styrene block copolymer 15–35 wt %, said rosin-based resin 10–25 wt %, and said plasticizer 30–60 wt %, and said 1-menthol 0.5–5 wt %.

7. A plaster according to claim 1, wherein a content of said 1-menthol weight is not more than one third of a content of said felbinac, wherein the content is in parts by weight.

8. A plaster according to claim 1, wherein said plasticizer is liquid paraffin.

9. A plaster according to claim 1, wherein said thickness of said plaster has a thickness of 80–200 μm.

10. A plaster according to claim 1, wherein said plaster further comprises 6–40 wt % of a polyisobutylene.

11. A plaster according to claim 1, wherein said plaster further comprises 0.1–5 wt % of an antioxidant.

12. A plaster consisting essentially of 10–40 wt % of a styrene-isoprene-styrene block copolymer, 5–30 wt % of a rosin-based resin, 20–70 wt % of a plasticizer, 0.01–7 wt % of 1-menthol, and 1.1–10 wt % of felbinac as a medicinally effective component, wherein said plaster does not contain crotamiton which is a solubilizer for said felbinac, said felbinac is uniformly dispersed in a semi-solubilized state in said plaster, wherein solubilized felbinac and microcrystalline felbinac coexist in said plaster, and said plaster has a thickness of 50–300 μm.

13. A plaster according to claim 2, wherein a content of said 1-menthol is not more than one third of a content of said felbinac, the content is in parts by weight.

* * * * *